United States Patent
Pasquet et al.

(10) Patent No.: US 7,879,073 B2
(45) Date of Patent: Feb. 1, 2011

(54) SELF-LOCKING DEVICE FOR FASTENING AN INTERVERTEBRAL IMPLANT

(75) Inventors: Denis Pasquet, Quinsac (FR); Régis Le Couedic, Andresy (FR)

(73) Assignee: Zimmer Spine, Bordeaux (FR)

( * ) Notice: Subject to any disclaimer, the term of this patent is extended or adjusted under 35 U.S.C. 154(b) by 668 days.

(21) Appl. No.: 11/579,989

(22) PCT Filed: May 9, 2005

(86) PCT No.: PCT/FR2005/001141
§ 371 (c)(1),
(2), (4) Date: Nov. 9, 2006

(87) PCT Pub. No.: WO2005/120277
PCT Pub. Date: Dec. 22, 2005

(65) Prior Publication Data
US 2007/0233081 A1 Oct. 4, 2007

(30) Foreign Application Priority Data
May 11, 2004 (FR) .................................. 04 05065

(51) Int. Cl.
*A61B 17/70* (2006.01)
(52) U.S. Cl. ....................... 606/249; 606/248
(58) Field of Classification Search ......... 606/246–249; 623/17.11–17.16; 24/197–198, 200
See application file for complete search history.

(56) References Cited

U.S. PATENT DOCUMENTS

| 5,245,731 | A | * | 9/1993 | Funathu ....................... 24/200 |
| 5,848,454 | A | * | 12/1998 | Kojima ........................ 24/200 |
| 7,087,083 | B2 | * | 8/2006 | Pasquet et al. ........... 623/17.11 |
| 7,238,204 | B2 | * | 7/2007 | Le Couedic et al. ...... 623/17.11 |
| 2005/0245929 | A1 | * | 11/2005 | Winslow et al. ............... 606/61 |

FOREIGN PATENT DOCUMENTS

WO   WO02071960   * 9/2002

* cited by examiner

*Primary Examiner*—Eduardo C Robert
*Assistant Examiner*—Steven J Cotroneo
(74) *Attorney, Agent, or Firm*—Seager, Tufte & Wickhem, LLC

(57) ABSTRACT

A locking device for locking two ties which may be coupled to an intervertebral spacer. The locking device includes a body having a first face for facing a wall of the intervertebral spacer, and a second face opposite the first face. The body includes an axial slot opening out into both faces of the body; two lateral slots, each lateral slot opening out into both faces and having dimensions suitable for allowing one tie to pass freely therethrough between opposing side surfaces of the lateral slot; and two presser surfaces defined in the first face, each presser surface extending between one end of the body and the nearer lateral slot. One side surface of each lateral slot converges with the associated presser surface to define a first edge, and the other side surface of each lateral slot converges with the second face to define a second edge.

7 Claims, 2 Drawing Sheets

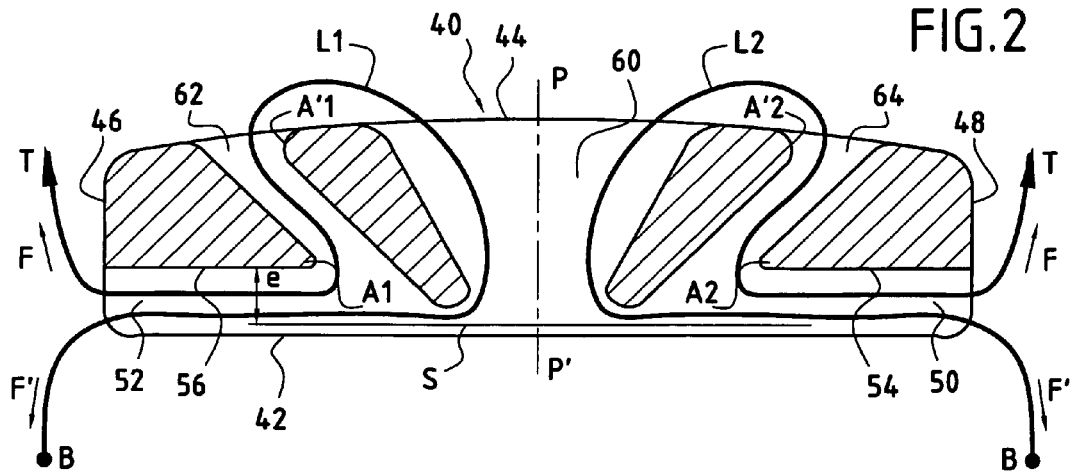
FIG.2
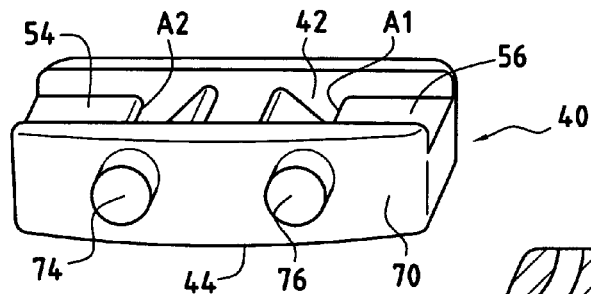
FIG.3
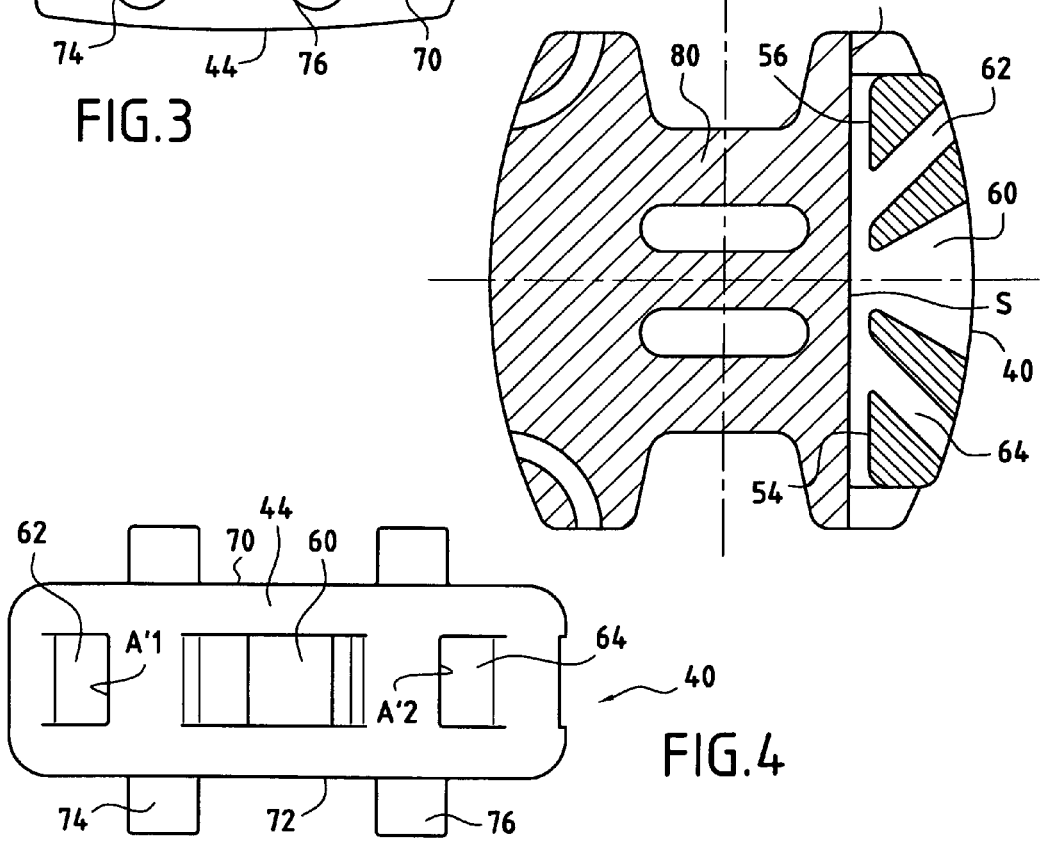
FIG.5
FIG.4

SELF-LOCKING DEVICE FOR FASTENING AN INTERVERTEBRAL IMPLANT

The present invention relates to a self-locking fastener device, in particular for fastening an intervertebral implant.

Intervertebral implants are essentially constituted by a spacer and by fastener means constituted by a braid or a tie in the form of a tape. The spacer is elongate in shape and is terminated at each end by a respective notch for receiving the spinous process of one of the two vertebrae that are to be connected together. The ties that are fastened to the spacer go round each of the spinous processes in order to secure the spacer to the two vertebrae.

In PCT patent application WO 02/071960 in the name of the Applicant, an intervertebral implant is described in which two self-locking devices are provided for fastening two ties.

Accompanying FIG. 1 shows an intervertebral implant of the type described in the above-mentioned patent application. FIG. 1 shows the spacer 10 with its two notches 12 and 14 that are to receive the spinous processes of the vertebrae V1 and V2.

To fasten the ties L1 and L2, two self-locking devices 16 and 18 are used that are secured, e.g. by clip-fastening, in recesses formed in the side walls 20 and 22 of the spacer 10. Each self-locking device 16 and 18 comprises a set of slots such as 24, 26, 28 through which one end of the tie L1 or L2 is caused to pass. The other end 30 of each tie is secured to the spacer by means of a loop 32. By pulling on the free end T of each tie L1 or L2, the tie is appropriately tightened around the spinous process V1 or V2, and the system 16 or 20 is self-locking insofar as when tension on the tie is released, the tie remains locked in the self-locking device.

Those two self-locking devices 16 and 18 present numerous advantages for the surgeon compared with the methods used in prior art spacers for fastening ties.

Nevertheless, in certain circumstances, the two self-locking devices shown in FIG. 1 can present drawbacks.

Usually, during the surgery proper, and regardless of whether it involves a stenosis or removing the intervertebral disk in full or part, the surgeon needs to take action on one side only of the patient's spinal column, thereby limiting the severity of the surgery. Nevertheless, it will be understood that because two self-locking devices are used, situated on either side of the spacer in order to tension both ties, it is nevertheless necessary for the surgeon to take action on both sides of the spinal column, taking care to leave sufficient space to be able to apply traction to the ends of both ties.

An object of the present invention is to provide a device that enables two ties or braids to be locked in the intervertebral implant without presenting the above-mentioned drawback.

According to the invention, this object is achieved by a device for locking two braids in the form of tapes and presenting a certain thickness, said device being for fastening on a wall of an element, and being characterized in that it is constituted by a body having a first face for facing the wall of said element and a second face opposite from the first face, said body presenting a plane of symmetry orthogonal to said first face, said body also presenting two ends disposed symmetrically about said plane, said plane further comprising:

an axial slot having said plane as its plane of symmetry, opening out into both faces of the body and having dimensions suitable for allowing both braids to pass freely;

two lateral slots disposed symmetrically relative to the plane of symmetry, each lateral slot opening out into both faces and having dimensions for allowing one braid to pass freely; and two presser surfaces defined in said first face of the body, each presser surface extending between one end of the body and the nearer lateral slot;

one flank of each lateral slot co-operating with the associated presser surface to define a first edge, and the other flank of each lateral slot co-operating with the second face of the body to define a second edge, said first edge being closer to the plane of symmetry than the second edge; and when said device is fastened on said element, the distance between the presser surfaces and the wall of said element is no greater than twice the thickness of a braid.

It will be understood that by means of the invention, a single self-locking device suffices to lock both braids of the intervertebral implant. With this single locking device being fastened on one of the side walls of the spacer, e.g. by clip-fastening, the surgeon needs to have access to one side only of the spacer, and thus of the spinal column, in order to ensure that both braids of the implant are locked.

Other characteristics and advantages of the invention appear better on reading the following description of a preferred embodiment of the invention given by way of non-limiting example. The description refers to the accompanying figures, in which:

FIG. 1, described above, is a vertical section view through a prior art intervertebral implant;

FIG. 2 is a longitudinal section view of the locking device of the invention;

FIG. 3 is a perspective view of the locking device of the invention;

FIG. 4 is an elevation view of the locking device of the invention;

FIG. 5 is a vertical section view showing a first example of the locking device in use mounted on the spacer of an intervertebral implant.

Figure 1:
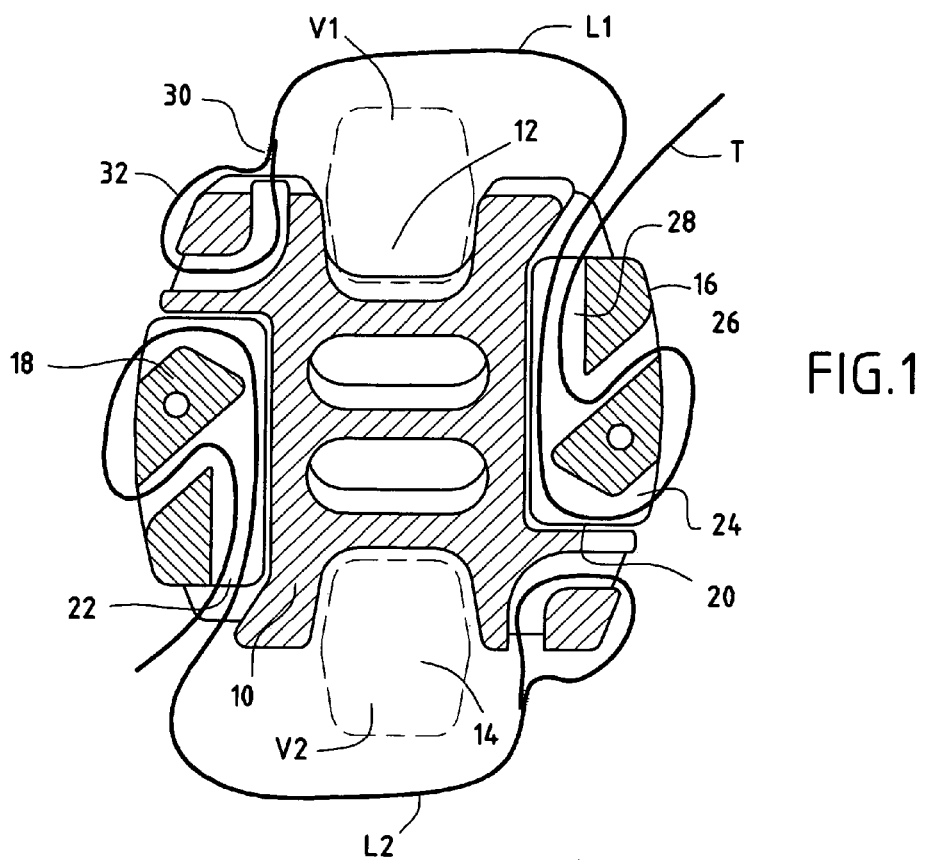

With reference initially to FIGS. 2 to 4, there follows a description of the dual locking device of the invention.

The dual locking device given overall reference 40 presents an inner first face 42, an outer face 44, and two end faces 46 and 48. There are two housings 50 and 52 in the inner face 42 that open out into the end faces 46 and 48 and that define two plane presser surfaces 54 and 56 parallel to the surface S of the element on which the locking device 40 is to be mounted. The presser surfaces 54 and 56 leave a gap of width e between themselves and the surface S. The locking device 40 also has an axial slot 60 of flared shape opening out into the outer face 44 and into the inner face 42. The device also has two inclined lateral slots 62 and 64 disposed symmetrically about the axial slot 60. Each of the lateral slots 62 and 64 also opens out into the outer face 44 and into the inner face 42 of the device. These slots flare away from the plane of symmetry P P' on going away from the inner face 42 towards the outer face 44.

The housings 50 and 52 and the lateral slots 62 and 64 define respective edges A1 and A2. The lateral slots 62 and 64 also co-operate with the outer face 44 of the device to define two edges A'1 and A'2.

FIG. 2 also shows the tie L1 with its end B that is secured to the spacer and its free end T on which traction can be exerted. There can also be seen the tie L2 which likewise has ends B and T. Each tie L1 and L2 penetrates into the device via housings 50 and 52 and then into the axial slot 60. Thereafter, the tie passes into one of the lateral sides 62 and 64 and finally into the housing 52 or 50 before exiting the locking device.

It should be specified that the edges A'1 and A'2 are further away from the midplane P P' of the locking device than are the edges A1 and A2. Thus, the link follows a Z-shaped path in its portion that passes through the lateral slots 62 and 64. Furthermore, the distance e between the surface S of the element on which the locking device is mounted and the presser surfaces 54 and 56 is at most about twice the thickness of the tie L1 or L2, such that the two strands of each tie passing through the housings 50 and 52 are clamped between the surface S and the presser surfaces 54 and 56.

It will be understood that when the surgeon exerts traction on the end T of a tie in the direction F, this traction tends to move the device 40 away from the surface S, thus allowing the two strands of the tie to slide freely between the surface S and the presser surface.

In contrast, during normal use of the locking device, any movement apart of the vertebrae tends to exert traction on the tie in the direction of arrow F'. This traction tends to move the presser surface closer to the surface S, thereby increasing the friction between the two strands of the tie passing through the housing 50 or 52. This effect is additional to the friction due to the edges A1, A'1 or A2, A'2, which friction is increased because of the relative positioning of the edges A1, A2 and A'1, A'2.

As can be seen more clearly in FIGS. 3 and 4, each side face 70 and 72 of the locking device is provided with clip-fastening studs 74, 76 suitable for co-operating with complementary clip-fastening members of the spacer. More generally, the locking device is provided with means for fastening on the element with which it is associated so that the appropriate distance is maintained between the surface S of the element and the presser surfaces 54 and 56.

FIG. 5 shows a first example of the dual self-locking device 40 mounted on an intervertebral spacer 80. In its side face 82, the spacer has a housing defining the surface S and having the device 40 mounted therein by clip-fastening.

Figure 6:
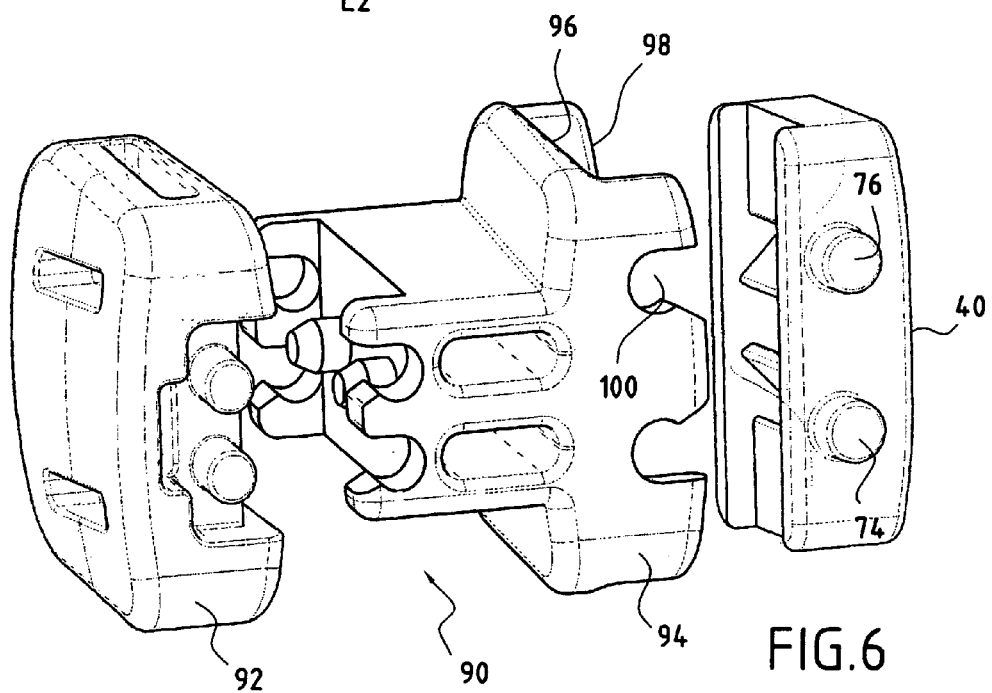
FIG. 6 is a perspective view showing a second example of the locking device in use mounted on a different intervertebral implant.

FIG. 6 shows a second example of the self-locking device 40 mounted on an intervertebral spacer 90. This spacer is itself constituted by two clip-fastenable parts 92 and 94. The face 96 (surface S) of the part 94 includes a housing 98 for receiving the self-locking device 40. This figure also shows the clip-fastening recesses 100 formed in the face of the part for co-operating with the clip-fastening studs 74 and 76.

Naturally, instead of having two distinct braids, the self-locking device could be used for fixing both ends of a single braid.

The invention claimed is:

1. A device for locking two ties each having a thickness, said device being for fastening on a wall of an element, in particular an intervertebral spacer, the device being constituted by a body having a first face for facing the wall of said element, and a second face opposite from the first face, said body presenting a plane of symmetry orthogonal to said first face, said body also presenting first and second opposing ends disposed symmetrically about said plane, the body further comprising:
   an axial slot having said plane as its plane of symmetry, opening out into both faces of the body and having dimensions suitable for allowing two ties to pass freely therethrough;
   first and second lateral slots disposed symmetrically about the plane of symmetry, each lateral slot opening out into both faces and having dimensions suitable for allowing one tie to pass freely therethrough between opposing side surfaces of the lateral slot; and
   first and second presser surfaces defined in said first face of the body, the first presser surface extending between the first end of the body and the first lateral slot, the second presser surface extending between the second end of the body and the second lateral slot;
   the first end, the first presser surface, and the first lateral slot are each disposed on a first side of the plane of symmetry, and the second end, the second presser surface, and the second lateral slot are each disposed on a second side of the plane of symmetry;
   one side surface of each lateral slot converging with the associated presser surface to define a first edge, and the other side surface of each lateral slot converging with the second face of the body to define a second edge, said first edge being closer to the plane of symmetry than the second edge;
   when said device is fastened on said element, the distance between the presser surfaces and the wall of said element is no greater than twice the thickness of a tie.

2. A device according to claim 1, wherein said axial slot flares towards the second face of the body.

3. A device according to claim 2, wherein each lateral slot is inclined, the end of the lateral slot opening out into the second face being further from the plane of symmetry than its end that opens out into the first face.

4. A device according to claim 1, wherein said presser surfaces are planar and parallel to the wall of said element.

5. A device according to claim 1, further comprising fastener means for fastening it on said element.

6. A device according to claim 5, wherein said fastener means are clip-fastener means.

7. A device according to claim 1, wherein said element is an intervertebral spacer.

* * * * *